United States Patent [19]

Cantin et al.

[11] Patent Number: 5,736,567
[45] Date of Patent: Apr. 7, 1998

[54] STABLE COMPOSITION CONTAINING ASCORBIC ACID

[75] Inventors: Hervé Cantin, Morangis; Eric Quemin, Villepinte; Didier Gagnebien, Chatillon; Isabelle Afriat, Paris, all of France

[73] Assignee: L'Oreal, Paris, France

[21] Appl. No.: 685,600

[22] Filed: Jul. 24, 1996

[30] Foreign Application Priority Data

Jul. 25, 1995 [FR] France .................................. 95 09026

[51] Int. Cl.$^6$ .................................................. A61K 31/34
[52] U.S. Cl. .................................................. 514/474
[58] Field of Search ............................ 549/315; 514/474

[56] References Cited

U.S. PATENT DOCUMENTS

| | | | |
|---|---|---|---|
| 4,818,521 | 4/1989 | Tamabuchi | 514/474 |
| 4,983,382 | 1/1991 | Wilmott et al. | 514/474 |
| 5,140,043 | 8/1992 | Darr et al. | 514/474 |
| 5,308,621 | 5/1994 | Taylor et al. | 514/474 |
| 5,314,686 | 5/1994 | Todd | 514/474 |
| 5,587,149 | 12/1996 | Punto et al. | 514/474 |

FOREIGN PATENT DOCUMENTS 19 22 653  11/1970  Germany .
27 44 976  4/1979  Germany .
WO-A-90
12572  11/1990  WIPO .

OTHER PUBLICATIONS

Database WPI Week 9205, Derwent Publications Ltd., London, GB; AN 92-035174 & JP-A-03 275 610.

Lee et al, *Journal of Food Science*, vol. 40, pp. 370-373 (1975).

Patent Abstract of Japan, vol. 4, No. 42 (C-5) [524] Feb. 6, 1980, 1980 & JP-A-55 017313.

Hajratwala, *Revue Sciences Pharmaceutiques*, 15 Mar. 1985, pp. 281-286.

*Primary Examiner*—James H. Reamer
*Attorney, Agent, or Firm*—Oblon, Spivak, McClelland, Maier & Neustadt, P.C.

[57] ABSTRACT

A composition for topical application is provided containing ascorbic acid and at least one polyol, the latter being present in an effective quantity to obtain a water activity value of the composition which is lower than or equal to 0.85, and at least one structuring agent chosen from polymers and oils, with a view to stabilizing the ascorbic acid. In such a composition ascorbic acid retains its effectiveness over the course of time. The composition obtained can be employed for treating and/or caring for the skin.

23 Claims, No Drawings

STABLE COMPOSITION CONTAINING ASCORBIC ACID

BACKGROUND OF THE INVENTION

1. Field of the Invention

The present invention relates to a composition for topical application, containing stabilized ascorbic acid, which can be employed, in particular, in the cosmetic and/or dermatological fields.

The invention also relates to a use of this composition for the cosmetic treatment of the skin and for the manufacture of a preparation intended for the dermatological treatment of the skin.

The invention further relates to a process of cosmetic treatment which consists in applying the composition to the skin. The composition of the invention may be applied topically to the face, including around the eyes, to the body and to the scalp of human beings.

2. Discussion of the Background

Attempts have been made for a long time to stabilize ascorbic acid, or vitamin C, in suitable galenic presentations, because of its beneficial properties.

In fact, ascorbic acid has many biological functions, such as the stimulation of the synthesis of collagen, reinforcement of cutaneous tissues against external attacks (UV radiation, pollution), depigmentation, activity against free radicals and compensation of vitamin E deficiency. Some of these beneficial properties have been reported, especially by England and Seifter, in the paper "The biochemical functions of ascorbic acid", published in Ann. Rev. Nutri., 1986, vol. 6, pp 365–406.

However, because of its chemical structure (an alpha-ketolactone), ascorbic acid is highly sensitive to the effects of environmental factors such as light, oxygen and water (due to its pH and due to the presence of traces of metals). This results in an unavoidable degradation of ascorbic acid in solution over the course of time. This problem has previously been treated in various ways.

To decrease or delay the degradation of ascorbic acid in solution, U.S. Pat. No. 5,140,043 discloses introducing it into hydroalcoholic solutions made up of at least 80% of water and which have a pH lower than 3.5. Because of the high acidity of these solutions, their use in the cosmetic and/or pharmaceutical field is difficult to envisage. In fact, a repeated application of these solutions can perturb the equilibrium of the skin and, in particular, can irritate or even burn the skin.

Furthermore, the paper by B. R. Hajratwala, entitled "Stability of ascorbic acid", published in the Revue Sciences Pharmaceutiques on 15 Mar. 1985, is known. In this article it is taught to stabilize ascorbic acid in acidic aqueous solution by adding a surface-active agent which is an oxyethylenated sorbitan ester. In addition, the article teaches the use of a chelating agent such as ethylenediaminetetraacetic acid (EDTA), and packaging under nitrogen, in the absence of light, to improve the stability of ascorbic acid in aqueous solution.

When applied to the skin, such an acidic aqueous solution exhibits the same disadvantages as those described above in the case of acidic hydroalcoholic solutions. In addition, the stabilization obtained is still insufficient.

Other methods of stabilization of ascorbic acid have been envisaged, especially using coatings (a technique described in FR-A-1600826) or by granulation of ascorbic acid (technique illustrated in JP-A-53-127819, for agri-foodstuffs application). However, these techniques are, on the one hand, costly and, on the other hand, can denature ascorbic acid, for example on heating, and/or can result in compositions which are not very cosmetic, as in the case of granulates.

The use of metal salts of phosphorylated ascorbic acid, especially magnesium ascorbyl phosphate, in cosmetic compositions is also known from FR-A-1489249. This latter compound has an activity close to that of the ascorbic acid from which it originates, but exhibits some disadvantages which make its use on the skin rather improbable. In particular, since magnesium ascorbyl phosphate is stable only at basic pH (pH 8 to pH 9), it must be incorporated into a basic composition which may be an irritant to the skin (the pH of which has a value of approximately 5.5).

Consequently, all the suggestions which have been made hitherto have not made it possible to solve the technical problems related to the instability of ascorbic acid in solution, in a suitable galenic form for the cosmetic and/or dermatological fields and at a cost that is compatible with industrial requirements. There is, therefore, a continuing need for a composition that can be employed in the cosmetic and/or dermatological fields, containing stabilized ascorbic acid in the free state, that is to say without any additional—in particular stabilizing—group and which does not cause any skin irritation after application.

SUMMARY OF THE INVENTION

It has now been unexpectedly found that the use of at least one water-binding polyol in a topical composition containing ascorbic acid, in an effective quantity for obtaining a water activity value of the composition which is lower than or equal to 0.85 and of at least one structuring agent, makes it possible to avoid the degradation of ascorbic acid.

DETAILED DESCRIPTION OF THE PREFERRED EMBODIMENTS

The subject of the present invention is a stable composition for topical application, containing ascorbic acid and at least one polyol, characterized in that the polyol is present in a quantity that is effective for obtaining a water activity value of the composition which is lower than or equal to 0.85, and in that the composition contains at least one structuring agent chosen from polymers and oils.

Preparing topical compositions based on ascorbic acid containing polyols is known, but it has never been described or suggested that the mere presence of polyol in a certain quantity and of a structuring agent can avoid the degradation of ascorbic acid. Thus, U.S. Pat. No. 5,140,043 encourages a person skilled in the art to employ a glycol concentration of between 20 and 40%, with a quantity of water at least equal to that of the glycols. On the other hand, it directs a person skilled in the art away from employing a glycol concentration of 60%.

However, it has now been found that polyols employed in a quantity such that the water activity value does not exceed 0.85 and in combination with a structuring agent can prevent the degradation of ascorbic acid.

The subject of the present invention is also the use, in a composition for topical application, containing ascorbic acid, of at least one polyol in a quantity that is effective for obtaining a water activity value of the composition which is lower than or equal to 0.85, and of at least one structuring agent chosen from polymers and oils, with a view to stabilizing the ascorbic acid. The polymer is preferably chosen from acrylic and methacrylic polymers.

The quantity of the polyol(s) must preferably be such that the water activity value of the composition is lower than or equal to 0.7.

The water activity $a_w$ of a mixture containing water is the ratio of the water vapor pressure of the product "product $P_{H2O}$" to the vapor pressure of pure water "pure $P_{H2O}$" at the same temperature. It can also be expressed as the ratio of the number of water molecules "$N_{H2O}$" to the total number of molecules "$N_{H2O}+N_{dissolved\ substance}$", which takes into account dissolved substances "$N_{dissolved\ substances}$".

It is given by the following formulae:

$$a_w = P_{H2O}\text{product}/P_{H2O}\text{pure} = N_{H2O}/(N_{H2O}+N_{dissolved\ substances})$$

Various methods can be employed for measuring the water activity. The most common one is the manometric method by which the vapor pressure is measured directly.

Conventionally a cosmetic or dermatological composition has a water activity of about 0.95 to 0.99. A water activity lower than 0.85 represents a marked decrease in the water activity, which means that the composition must have a minimum quantity of water and in any case lower than that of the polyol(s).

The polyol employed according to the invention may be chosen especially from glycerin and glycols, preferably poly($C_{2-4}$ alkylene) glycols and glycols containing 3–10 carbon atoms, in particular propylene glycol and polyethylene glycols. Preferred polyethylene glycols have a weight average molecular weight in the range from about 50 to about 600 g/mole.

The quantity of the polyol or polyols to be used is dependent on the type of compositions (gel or emulsion) and on the other constituents of the composition. This quantity must be sufficient to achieve a suitable water activity. The polyol or polyols used according to the invention are preferably present in a quantity of at least 30% by weight, preferably ranging from 30 to 99.99% by weight, and, more preferably, from 45 to 80% by weight, relative to the total weight of the composition.

A proportion of the polyol may be optionally replaced with an acrylic or methacrylic polymer containing one or more polyols and water in complexed or bound form.

An acrylic or methacrylic polymer is intended to mean a homopolymer or copolymer of acrylic or methacrylic acid or a homopolymer or copolymer of a derivative of acrylic or methacrylic acid. Preferred acrylic and methacrylic acid derivatives are the esters of these acids with suitable alcohols containing, for example, 1–10 carbon atoms and 1 or more, preferably 1–3 hydroxyl groups. The amount of acrylic or methacrylic acid in the copolymer can be widely varied and is not particularly limiting so long as the properties of the composition of the invention are retained.

The quantity of such polymers with the polyols and bound water, in the composition according to the invention, preferably ranges from 40 to 99.99% by weight and, more preferably, from 60 to 90% by weight, relative to the total weight of the composition.

As a homopolymer of this type there may be mentioned those sold under the names of NORGEL and LUBRAJEL CG by the Guardian company. These polymers are polyglyceryl acrylates complexed with more than 65% of glycerin and/or propylene glycol and less than 35% by weight of bound water.

In the composition according to the invention the ascorbic acid may be employed advantageously in a quantity ranging from 0.05 to 10% by weight, preferably from 0.5 to 5% by weight, relative to the total weight of the composition.

As oils which can be used in the invention, mention may be made of mineral oils (liquid petroleum), vegetable oils (jojoba oil), animal oils, synthetic oils (decyl oleate), silicone oils (cyclomethicone, polydimethylsiloxane, dimethicone) and fluorinated oils (perfluoropolyethers). The oil or oils can be present in a quantity ranging from 5 to 60%, and preferably from 5 to 40%, by weight relative to the total weight of the composition.

In addition, the composition according to the invention can contain one or more salts whose presence will further improve the stability of the ascorbic acid present therein.

Salts which may be mentioned in particular are magnesium salts and sodium salts and more especially magnesium sulfate, magnesium chloride and sodium chloride. The salt or salts can be present in a quantity ranging from 0.1 to 30% and preferably from 2 to 12% by weight, relative to the total weight of the composition.

The composition according to the invention contains a medium which is topically acceptable, that is to say compatible with the skin, and constitutes especially compositions for the protection, treatment or care of the skin.

Accordingly, another object of the invention is the use of the above composition for the cosmetic treatment of the skin and in particular for smoothing out the small wrinkles in the skin, toning it up, regenerating it, for lightening the complexion, removing the pigmentary spots from the skin, for combating the detrimental effects of the UV radiations, and/or for generally reinforcing the cutaneous tissues against the attacks of the environment (pollution).

Another object of the invention is the use of the above composition for the manufacture of a preparation intended for a dermatological treatment.

Finally, a further object of the invention is a process of cosmetic treatment which includes applying to the skin, including around the eyes, a composition in accordance with the invention.

The composition according to the invention can be presented especially in the form of a solution, a gel or a water-in-oil or oil-in-water emulsion constituting creams, ointments, lotions or milks. This composition may also include microcapsules, microparticles or vesicular dispersions of ionic and/or nonionic type. These various forms of composition are prepared by the usual methods.

When the composition of the invention is an emulsion, the proportion of the fatty phase may range from 10 to 80% by weight and preferably from 20 to 40% by weight, relative to the total weight of the composition. The emulsion preferably comprises at least one dispersant chosen from emulsifiers, vesicles and particles. The oils, emulsifiers and optionally the coemulsifiers which are employed in the composition in the form of emulsion are chosen from those conventionally employed in the cosmetic and dermatological fields. The emulsifier and the coemulsifier are present in the composition, for example, in a proportion ranging from 1 to 10% by weight and preferably from 2 to 6% by weight, relative to the total weight of the composition.

In addition to the abovementioned oils, the fatty phase may comprise fatty substances such as fatty alcohols, fatty acids (stearic acid) or waxes (silicone wax).

In a known manner the composition of the invention may also contain adjuvants which are conventional in the cosmetic and dermatological fields, such as surfactants, especially foaming surfactants, hydrophilic or lipophilic active agents in addition to ascorbic acid, gelling agents, preserving agents, antioxidants, chelating agents, solvents, perfumes, fillers, screening agents, odor absorbers and colorants. The quantities of these various adjuvants are those conventionally employed in the fields in question and, for example, from 0.01 to 15% of the total weight of the composition. Depending on their nature, these adjuvants may be introduced into the fatty phase, into the aqueous phase and/or into the lipid vesicles.

Emulsifiers that can be employed in the invention which may be mentioned are, for example, silicone emulsifiers such as the alkyldimethicone copolyols including the cetyldimethicone copolyol sold by the Goldschmidt company under the trade name ABIL EM-90, or the mixture of dimethicone copolyol and cyclomethicone, sold by the Dow Corning company under the name 3225C FORMULATION AID.

Hydrophilic active substances which may be employed include proteins or protein hydrolysates, amino acids, urea, allantoin, sugars and sugar derivatives, starch and bacterial or plant extracts, especially of Aloe vera.

Tocopherol (vitamin E) and its derivatives, retinol (vitamin A) and its derivatives, essential fatty acids, ceramides and essential oils may be employed as lipophilic active substances.

EXAMPLES

Test for stability of the activity of ascorbic acid:

The stability of ascorbic acid at a concentration of 2% and 5% in NORGEL was determined after 2 months at various temperatures.

| Gel | Ascorbic acid at $T_0$ | Ascorbic acid at $T_{2\ months}$ at 5° C. | Ascorbic acid at $T_{2\ months}$ at 20° C. | Ascorbic acid at $T_{2\ months}$ at 45° C. |
|---|---|---|---|---|
| Gel containing 2% of ascorbic acid | 2.05 ± 0.02% | 2.09 ± 0.01% | 2.09 ± 0.01% | 1.94 ± 0.01% |
| Gel containing 5% of ascorbic acid | 4.94 ± 0.03% | 5.07 ± 0.01% | 5.00 ± 0.05% | 4.52 ± 0.04% |

The stability of ascorbic acid after two months at 5° C. or at ambient temperature was very good. It was still satisfactory after two months at 45° C.

The following examples of compositions according to the invention are given by way of illustration and without any limitation being implied. The quantities therein are given in % by weight.

Example 1: Gel

NORGEL 85%
Ascorbic acid 1%
Water up to 100%

A translucent gel was obtained, which may be applied daily to the spots on the face and neck with a view to reducing them. The water activity was 0.65±0.02.

Example 2: Water-In-Oil Emulsion (a) Oily phase:
Cetyldimethicone copolyol (ABIL EM-90 sold by the Goldschmidt company) (emulsifier) 2%
Jojoba oil 4%
Liquid paraffin 10%
Polydimethylsiloxane 8%

(b) Aqueous phase:
Glycerin 48.6%
NaCl 0.5%
Ascorbic acid 0.5%
Water 26.4%

The procedure for preparing the emulsion was the following: the aqueous phase, on the one hand, and the oily phase, on the other hand, were prepared and the aqueous phase was emulsified in the oily phase at ambient temperature with stirring using a homogenizer.

A white cream was obtained which was suitable for making it easier to smooth out the blemishes of the skin. The water activity was 0.63±0.02.

Example 3: Water-In-Oil Emulsion (a) Oily phase:
Dimethicone copolyol and cyclomethicone ("3225C FORMULATION AID" sold by Dow Corning) 22.6%
Dimethicone 5%
Mineral oil 3%

(b) Aqueous phase:
Glycerin 37%
Magnesium sulphate (stabilizer) 2%
Propylene glycol 7%
Ascorbic acid 1%
Water 22.4%

The emulsion was prepared in the same way as in Example 2. A white cream was obtained, the application of which to the skin gave a radiant complexion. The water activity was 0.63±0.02.

Example 4: Water-In-Oil Emulsion (a) Oily phase:
Dimethicone copolyol and cyclomethicone ("3225C FORMULATION AID" sold by Dow Corning) 8%
Phenyltrimethylsiloxytrisiloxane ("556 FLUID" sold by Dow Corning) 15%
Tocopherol 0.5%

(b) Aqueous phase:
Propylene glycol 39.4%
Polyethylene glycol 400 13%
Disodium salt of ethylenediaminetetraacetic acid (chelating agent) 0.1%
Ascorbic acid 3%
Water 21%

The emulsion was prepared in the same way as in Example 2. A white cream was obtained, the application of which to the skin gave a radiant complexion. The water activity was 0.63±0.02.

Example 5: Water-In-Oil Emulsion (a) Oily phase:
Dimethicone copolyol and cyclomethicone ("3225C FORMULATION AID" sold by Dow Corning) 8%
Phenyltrimethylsiloxytrisiloxane ("556 FLUID" sold by Dow Corning) 15%
Tocopherol 0.5%

(b) Aqueous phase:
Propylene glycol 32.4%
Polyethylene glycol 400 13%
Disodium salt of ethylenediaminetetraacetic acid (chelating agent) 0.1%
Ascorbic acid 3%
Water 28%

The emulsion was prepared in the same way as in Example 2. A white cream was obtained, the application of which to the skin gave a radiant complexion. The water activity was 0.73±0.02.

Comparative Example 5: Water-In-Oil Emulsion (a) Oily phase:
Dimethicone copolyol and cyclomethicone ("3225C FORMULATION AID" sold by Dow Corning) 8%
Phenyltrimethylsiloxytrisiloxane ("556 FLUID" sold by Dow Corning) 15%

Tocopherol 0.5%
(b) Aqueous phase:
  Disodium salt of ethylenediaminetetraacetic acid (chelating agent) 0.1%
  Ascorbic acid 3%
  Water 28%

The emulsion was prepared in the same way as in Example 2. The water activity was 0.95±0.02.

The stability of ascorbic acid in the compositions of Examples 4 and 5 and of Comparative Example 5 was determined. The results presented in the following table show that the compositions of Examples 4 and 5 permit a good maintenance of the activity of ascorbic acid, which is not the case with the composition of Comparative Example 5:

| Composition | % degradation of ascorbic acid at $T_{2\ months}$ at 5° C. | % degradation of ascorbic acid at $T_{2\ months}$ at 20° C. | % degradation of ascorbic acid at $T_{2\ months}$ at 45° C. |
| --- | --- | --- | --- |
| Example 4 ($a_w = 0.63$) | 0% | 0.7% | 3.3% |
| Example 5 ($a_w = 0.73$) | 0% | 3.5% | 8% |
| Comparative Example 5 ($a_w = 0.95$) | 0% | 6.2% | 43% |

These results show that the degradation of ascorbic acid is proportionately greater the higher the water activity of the composition.

French Priority Document FR 95-09026 is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A composition, comprising ascorbic acid dissolved in water and at least one polyol forming an aqueous phase, wherein said polyol is present in a quantity that is effective for obtaining a water activity value of the composition which is lower than or equal to 0.85, the quantity of water in the composition being less than that of the polyol, and said composition comprises at least one structuring agent which is an oil present in a quantity ranging from 5 to 60% by weight, relative to the total weight of the composition.

2. The composition according to claim 1, wherein said oil is selected from the group consisting of mineral oils, vegetable oils, animal oils, synthetic oils, silicone oils and fluorinated oils.

3. The composition according to claim 2 in the form of an emulsion containing the oil in an oil phase, and further comprising at least one dispersant selected from the group consisting of emulsifiers, vesicles and particles.

4. The composition according to claim 3, wherein the emulsion is a water-in-oil emulsion.

5. The composition according to claim 1, wherein the quantity of water added as such in the formulation of the composition is at least 14% by weight of the total composition.

6. The composition according to claim 1, wherein the quantity of water in the composition is at least 21% by weight of the total composition.

7. The composition according to claim 1, wherein the quantity of water in the aqueous phase is at least 27.5% by weight of the aqueous phase.

8. The composition according to claim 1, wherein the quantity of water in the aqueous phase is at least 40% by weight of the polyol in the aqueous phase.

9. The composition according to claim 1, wherein said polyol is present in a quantity that is effective for obtaining a water activity value of the composition which is lower than or equal to 0.7.

10. The composition according to claim 1, wherein said polyol is selected from the group consisting of glycerin and glycols.

11. The composition according to claim 1, further comprising at least one inorganic salt.

12. The composition according to claim 11, wherein said inorganic salt is selected from the group consisting of magnesium salts, calcium salts and sodium salts.

13. The composition according to claim 3, further comprising an inorganic salt present in a quantity ranging from 0.1 to 30% by weight, relative to the total weight of the emulsion.

14. The composition according to claim 1, wherein said ascorbic acid is present in a concentration ranging from 0.05 to 10% by weight, relative to the total weight of the composition.

15. The composition according to claim 1, further comprising at least one lipophilic or hydrophilic adjuvant selected from the group consisting of preserving agents, antioxidants, chelating agents, perfumes, fillers, screening agents, sequestrants, essential oils, colorants, hydrophilic and lipophilic active substances and lipid vesicles.

16. A composition, comprising ascorbic acid dissolved in water and at least one polyol forming an aqueous phase, wherein said polyol is present in a quantity that is effective for obtaining a water activity value of the composition which is lower than or equal to 0.85, the quantity of water in the composition being less than that of the polyol, and said composition comprises at least one structuring agent which is a polymer selected from the group consisting of homopolymers and copolymers of acrylic and methacrylic acid and homopolymers and copolymers of esters of acrylic and methacrylic acid.

17. The composition according to claim 16, wherein said polymer further comprises bound water.

18. The composition according to claim 17, wherein said polymer, said polyol and said bound water are present in a quantity ranging from 70 to 99.99% by weight, relative to the total weight of the composition.

19. The composition according to claim 16, wherein said polyol is present in a quantity that is effective for obtaining a water activity value of the composition which is lower than or equal to 0.7.

20. The composition according to claim 16, wherein said polyol is selected from the group consisting of glycerin and glycols.

21. The composition according to claim 16, further comprising at least one inorganic salt.

22. The composition according to claim 16, wherein said ascorbic acid is present in a concentration ranging from 0.05 to 10% by weight, relative to the total weight of the composition.

23. The composition according to claim 16, wherein the composition contains water added as such in an amount of at least 14% of the total weight of the composition.

* * * * *